(12) United States Patent
Chappo et al.

(10) Patent No.: US 9,316,751 B2
(45) Date of Patent: Apr. 19, 2016

(54) IMAGING DETECTOR WITH ANTI-ALIASING FILTER IN THE READOUT ELECTRONICS AND/OR PHOTOSENSOR

(71) Applicant: KONINKLIJKE PHILIPS N.V., Eindhoven (NL)

(72) Inventors: Marc Anthony Chappo, Elyria, OH (US); Randall Peter Luhta, Chardon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/390,798

(22) PCT Filed: Apr. 15, 2013

(86) PCT No.: PCT/IB2013/052980
§ 371 (c)(1),
(2) Date: Oct. 6, 2014

(87) PCT Pub. No.: WO2013/164720
PCT Pub. Date: Nov. 7, 2013

(65) Prior Publication Data
US 2015/0060681 A1    Mar. 5, 2015

Related U.S. Application Data

(60) Provisional application No. 61/640,029, filed on Apr. 30, 2012.

(51) Int. Cl.
*G01T 1/29* (2006.01)
*H01L 27/146* (2006.01)
*G01N 23/04* (2006.01)

(52) U.S. Cl.
CPC ............ *G01T 1/2928* (2013.01); *G01N 23/046* (2013.01); *H01L 27/1464* (2013.01);
(Continued)

(58) Field of Classification Search
CPC ..... H01L 27/146; G01T 1/2928; G01N 23/046
USPC ....................... 250/370.09, 395, 394
See application file for complete search history.

(56) References Cited

U.S. PATENT DOCUMENTS

| 4,158,133 A | 6/1979 | Spaeth et al. |
| 5,801,430 A | 9/1998 | Forrest et al. |

(Continued)

FOREIGN PATENT DOCUMENTS

| CN | 101937094 A | 1/2011 |
| EP | 1206125 A2 | 5/2002 |

OTHER PUBLICATIONS

Canfield, L. R., et al.; Silicon photodiodes with integrated thin film filters for selective bandpasses in the extreme ultraviolet; 1994; SPIE Ultraviolet Technology; vol. 2282:31-38.

(Continued)

*Primary Examiner* — David Porta
*Assistant Examiner* — Faye Boosalis

(57) ABSTRACT

An imaging apparatus (400) includes a detector array (412) with at least one detector tile (418). The detector tile includes a photosensor array (422) with a two dimensional array of individual photosensitive detector pixels (424) located within a non-photosensitive area (426). The imaging apparatus also includes readout electronics (432) coupled to the photosensor array and including individual readout channel wells (602, 604) corresponding to the individual detector pixels. The imaging apparatus also includes an anti-aliasing filter (800) for a detector pixel that is located in at least one of a region of the photosensor array corresponding to the detector pixel or a region of the readout electronics corresponding to the detector pixel.

20 Claims, 8 Drawing Sheets

(52) U.S. Cl.
CPC ...... *H01L27/1469* (2013.01); *H01L 27/14634* (2013.01); *H01L 27/14661* (2013.01); *H01L 27/14663* (2013.01)

(56) References Cited

U.S. PATENT DOCUMENTS

| | | | |
|---|---|---|---|
| 6,510,195 | B1 | 1/2003 | Chappo et al. |
| 2003/0127672 | A1 | 7/2003 | Rahn et al. |
| 2007/0241260 | A1 | 10/2007 | Jaeger et al. |
| 2008/0237633 | A1 | 10/2008 | Jaeger et al. |
| 2009/0121146 | A1 | 5/2009 | Luhta et al. |
| 2010/0140732 | A1 | 6/2010 | Eminoglu et al. |
| 2011/0156197 | A1 | 6/2011 | Tivarus et al. |
| 2012/0061789 | A1 | 3/2012 | Yang et al. |

OTHER PUBLICATIONS

Steadman, R., et al.; A CMOS photodiode array with in-pixel data acquisition system for computed tomography; 2004; IEEE Journal of Solid-State Circuits; 39(7)1034-1043.

IMAGING DETECTOR WITH ANTI-ALIASING FILTER IN THE READOUT ELECTRONICS AND/OR PHOTOSENSOR

CROSS REFERENCE TO RELATED APPLICATIONS

This application is a national filing of PCT application Serial No. PCT/IB2013/052980, filed Apr. 15, 2013, published as WO 2013/164720 A1 on Nov. 7, 2013, which claims the benefit of U.S. provisional application Ser. No. 61/640,029 filed Apr. 30, 2012, which is incorporated herein by reference.

The following generally relates to an imaging detector and more particularly to an imaging detector with anti-aliasing filter in the readout electronics and/or photosensor and is described in connection with computed tomography (CT).

A CT scanner generally includes an x-ray tube mounted on a rotatable gantry that rotates around an examination region about a z-axis. The x-ray tube emits radiation that traverses the examination region. A detector array subtends an angular arc opposite the examination region from the x-ray tube, detects radiation that traverses the examination region, and generates a signal indicative thereof. A reconstructor processes the signal and reconstructs volumetric image data indicative thereof the examination region and a portion of a subject or object located therein during scanning.

The CT detector array described in U.S. Pat. No. 6,510,195 to Chappo et al. includes one or more rows of detector tiles. Each detector tile includes a scintillator layer optically coupled to a two-dimensional (2D) back-illuminated photodiode array of detector pixels (e.g., 16 or more). The photodiode array is bonded on a carrier substrate via bump bonding. Readout electronics packaged in an application specific integrated chip (ASIC) are also bonded on the carrier substrate. The carrier substrate includes electrodes that route signals produced by the detector pixels to the readout electronics.

In U.S. patent application publication 2009/0121146 to Luhta et al., the CT detector tile includes a silicon photodiode with a photosensitive area and a non-photosensitive area. With this tile, the photodiode array is part of a photosensitive area of the silicon substrate, and the non-photosensitive area includes electrodes that inter-connect each detector pixel to bonding pads. A silicon ASIC is directly bonded to the non-photosensitive area of the silicon substrate in electrical communication with the bonding pads and hence the detector pixels.

The ASIC includes readout electronics for each detector pixel, including analog and digital electronics for each detector pixel. FIG. 1 shows a portion of an example prior art ASIC 102, which includes first readout electronics 104 for a first detector pixel and second readout electronics 106 for a second different pixel. The first readout electronics 104 includes first analog components 108 and first digital components 110, and the second readout electronics 106 includes second analog components 114 and second digital components 116. The ASIC 102 also includes common digital electronics 112 including common digital components 118.

Note that the dashed lines around the components 108-118 do not indicate physical structure of the ASIC 102 but are included to clarify the illustrated groupings of the readout electronics components between analog, digital and common digital and between pixels. Unfortunately, the analog and digital readout electronics 108-118 are in a same substrate 120 and are therefore susceptible to substrate noise. In addition, the analog and digital readout electronics 110-118 are in the same substrate 120 and therefore the analog readout electronics 108 and 114 are susceptible to noise from the digital readout electronics 110, 116 and 118 and vice versa.

One approach to mitigating noise contamination is to electrically isolate the analog and digital readout electronics and from the substrate and each other. This has been done through CMOS triple-well or shallow trench isolation, as shown in FIG. 2. In FIG. 2, a first well 202 electrically isolates the analog readout electronics 108 and 114 from the substrate 120 and the digital readout electronics 110, 116 and 118, and a second well 204 electrically isolates the digital readout electronics 110, 116 and 118 from the substrate 120 and the analog channels 108 and 114. However, this approach does not mitigate crosstalk between the readout electronics in a same well and such crosstalk can negatively affect detector linearity, gain, and noise performance, and limit low-dose imaging.

Anti-aliasing filtering has been used in connection with the detector to reduce quantum noise and electronics noise by limiting the bandwidth of the signal before processing by the ASIC. Such anti-aliasing filtering has been implemented through single or a multiple order low-pass filter. One passive second order implementation is shown in FIG. 3, where an anti-aliasing filter 300 includes resistors 302 and 304, capacitors 306 and 308, an input electrode 310, and an output electrode 312. The filtered signal is subsequently routed to the ASIC 102 for processing. Unfortunately, such a filter increases the overall footprint of the electronics and may provide less than adequate anti-aliasing filtering, which may limit low noise performance and low dose imaging when undesired higher frequency noise components remain in the filtered signal. Active filters can also be utilized with additional area, power and cost.

In view of at least the above, there is unresolved need for other anti-aliasing filter configurations.

Aspects described herein address the above-referenced problems and/or others.

In one aspect, an imaging apparatus includes a detector array with at least one detector tile. The detector tile includes a photosensor array with a two dimensional array of individual photosensitive detector pixels located within a non-photosensitive area. The imaging apparatus also includes readout electronics coupled to the photosensor array and including individual readout channel wells corresponding to the individual detector pixels. The imaging apparatus also includes an anti-aliasing filter for a detector pixel that is located in at least one of a region of the photosensor array corresponding to the detector pixel or a region of the readout electronics corresponding to the detector pixel.

In another aspect, a method includes routing a detector pixel output signal to readout electronics corresponding to the detector pixel, which is one of a plurality of detector pixels in a photosensor array of an imaging detector, through an anti-aliasing filter that is located in one of the photosensor array or the readout electronics, wherein the readout electronics of the detector pixel are located in a well corresponding to the detector pixel and processing the signal with the readout electronics.

In another aspect, an imaging detector array includes a photosensor array with a two dimensional array of individual photosensitive detector pixels located within a non-photosensitive area. The imaging detector array further includes readout electronics coupled to the photosensor array, the readout electronics comprising: individual readout channel wells, each well corresponding to an individual detector pixel. The imaging detector array further includes an anti-aliasing filter for an individual readout channel well located in one of the photosensor array or the readout electronics.

The invention may take form in various components and arrangements of components, and in various steps and arrangements of steps. The drawings are only for purposes of illustrating the preferred embodiments and are not to be construed as limiting the invention.

Figure 5:
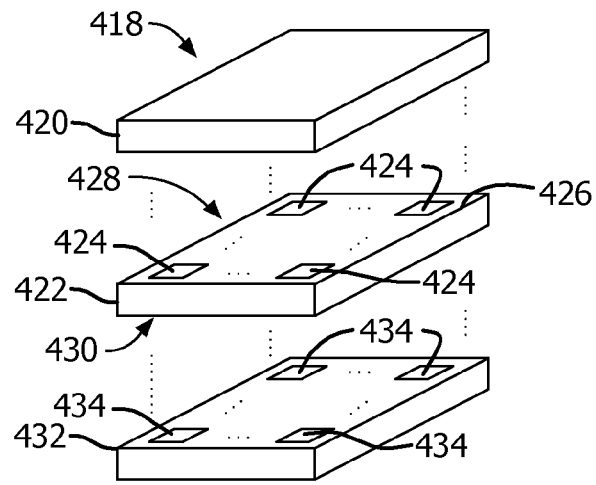

FIG. 5 schematically illustrates an example of the detector tile.

Figure 6:
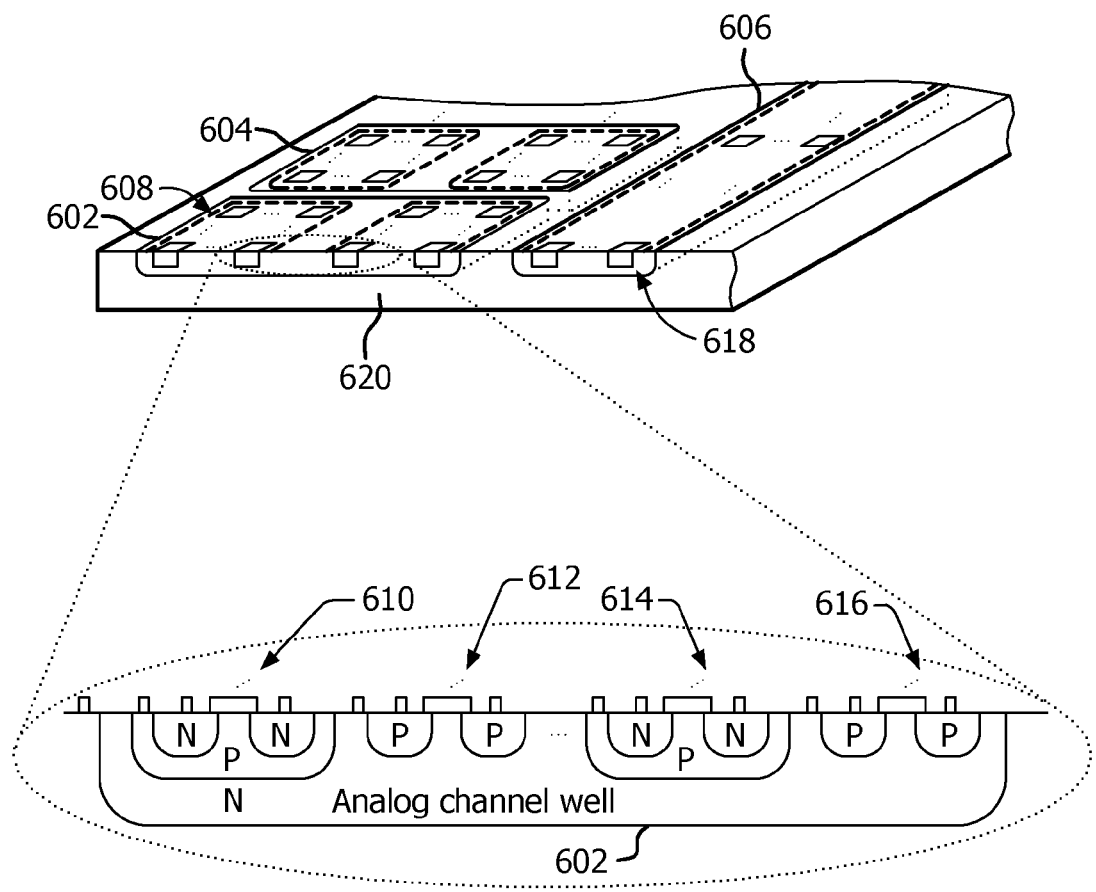

FIG. 6 schematically illustrates an example of the detector tile in which analog and digital readout electronics for each detector pixel are located in a corresponding analog channel well.

Figure 7:
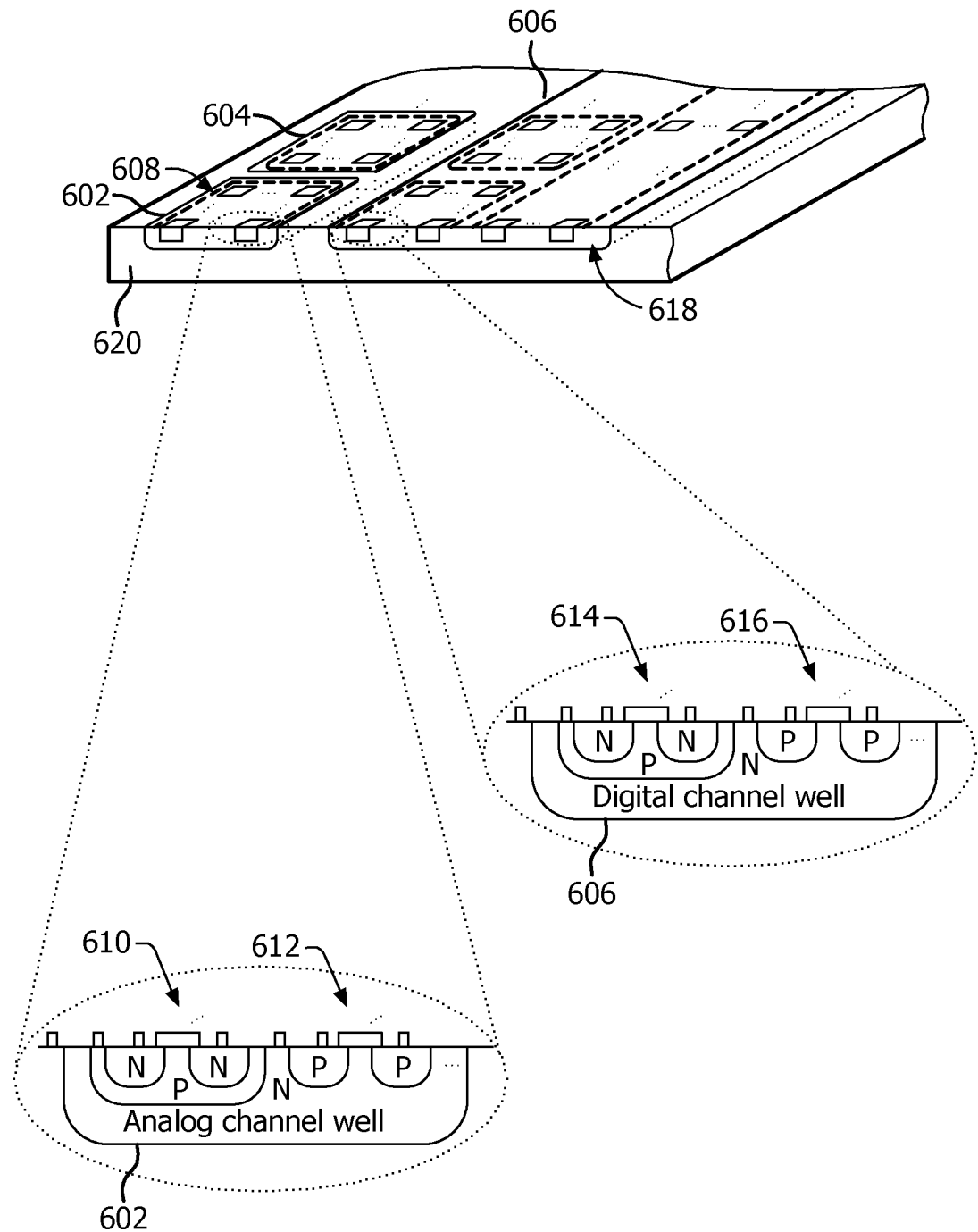

FIG. 7 schematically illustrates a variation of FIG. 6 in which the analog and the digital readout electronics of a pixel are located in different wells.

Figure 8:
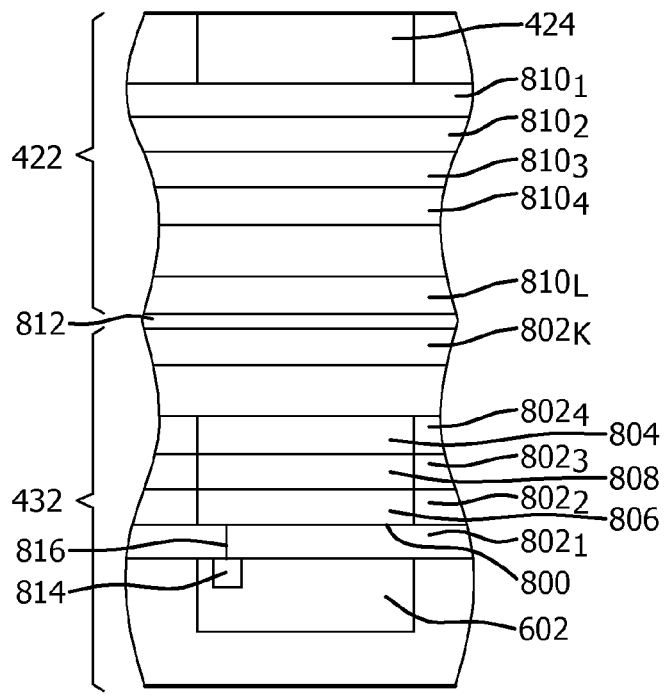

FIG. 8 schematically illustrates an example detector tile in which anti-aliasing circuitry is located in the layers of the readout electronics.

Figure 9:
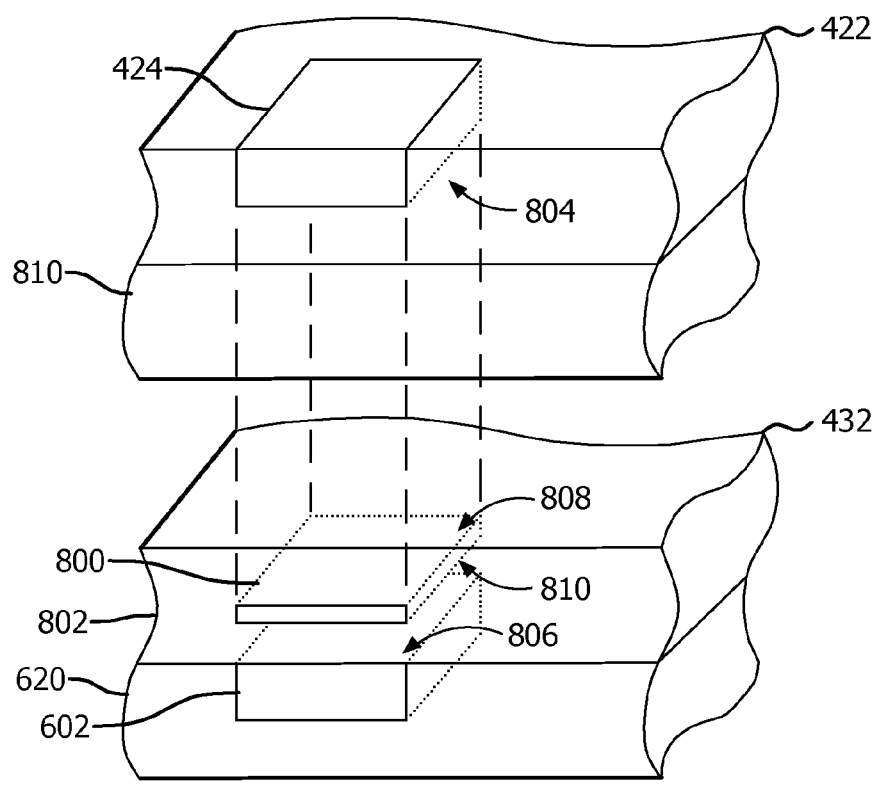

FIG. 9 illustrates a perspective view of the detector tile of FIG. 8, showing the geometrical relationship between the anti-aliasing circuitry, an individual pixel channel well, and an individual detector pixel.

Figure 10:
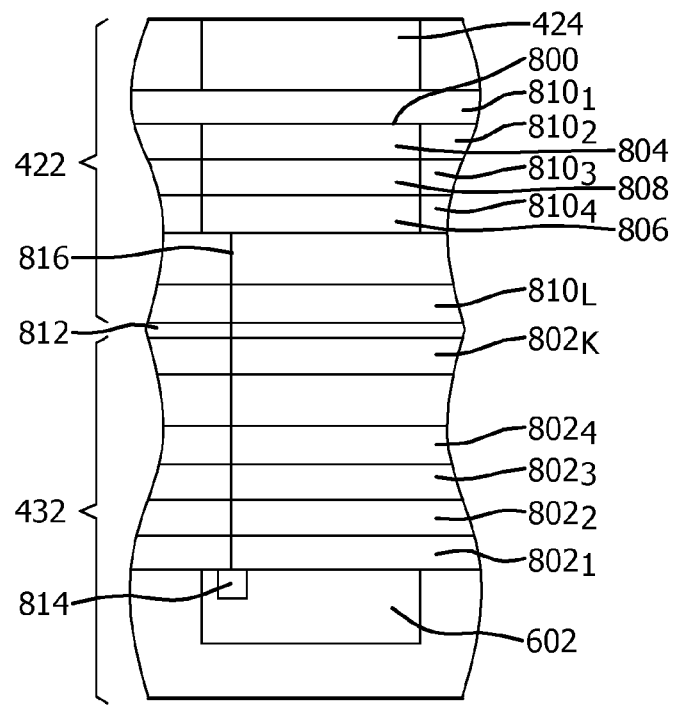

FIG. 10 schematically illustrates an example detector tile in which anti-aliasing circuitry is located in the layers of the photosensor.

Figure 11:
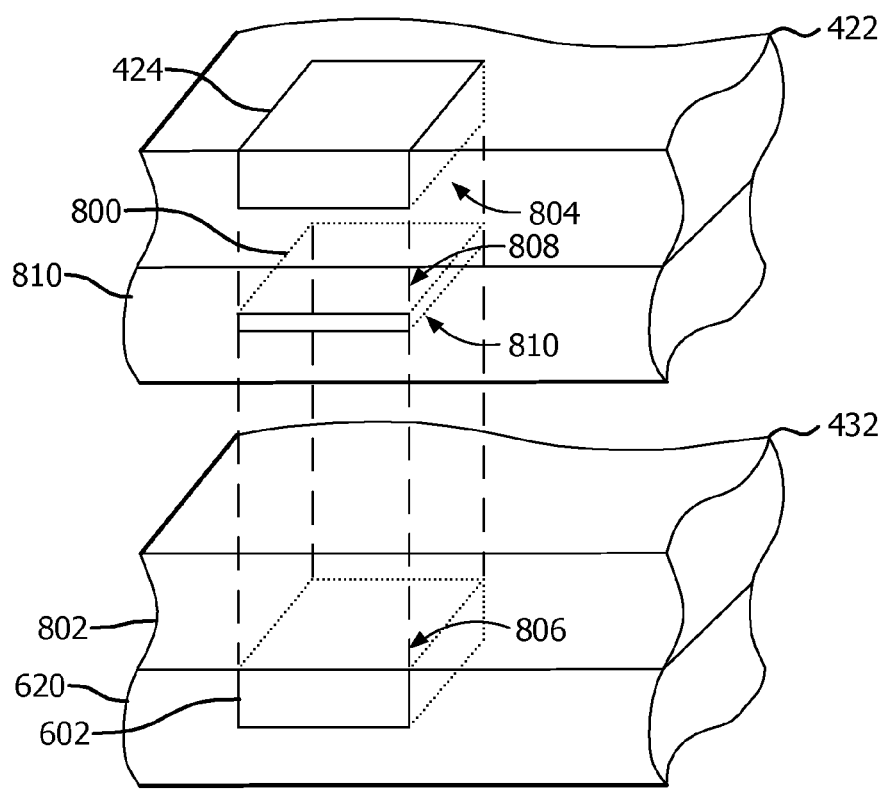

FIG. 11 illustrates a perspective view of the detector tile of FIG. 10, showing the geometrical relationship between the anti-aliasing circuitry, an individual pixel channel well, and an individual detector pixel.

Figure 12:
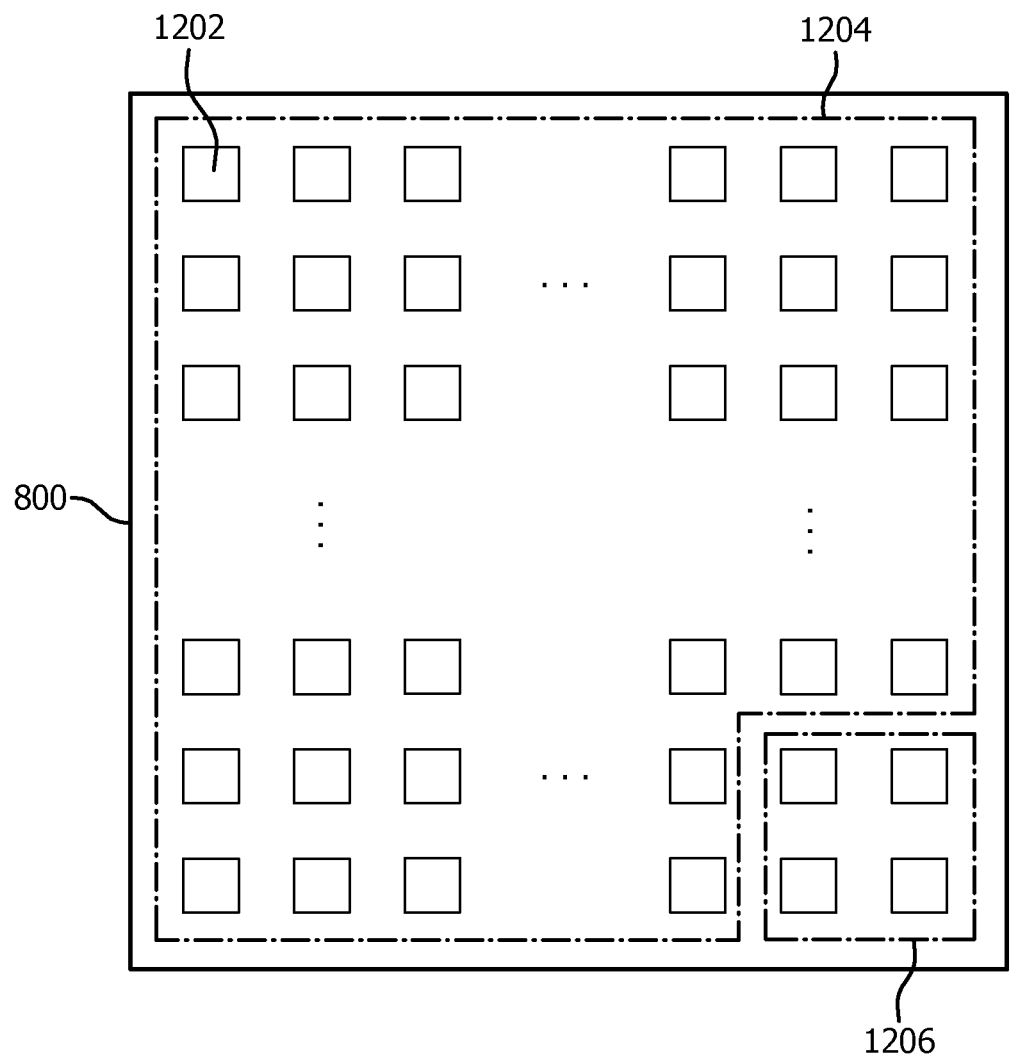

FIG. 12 illustrates an example configuration of the anti-aliasing circuitry.

Figure 13:
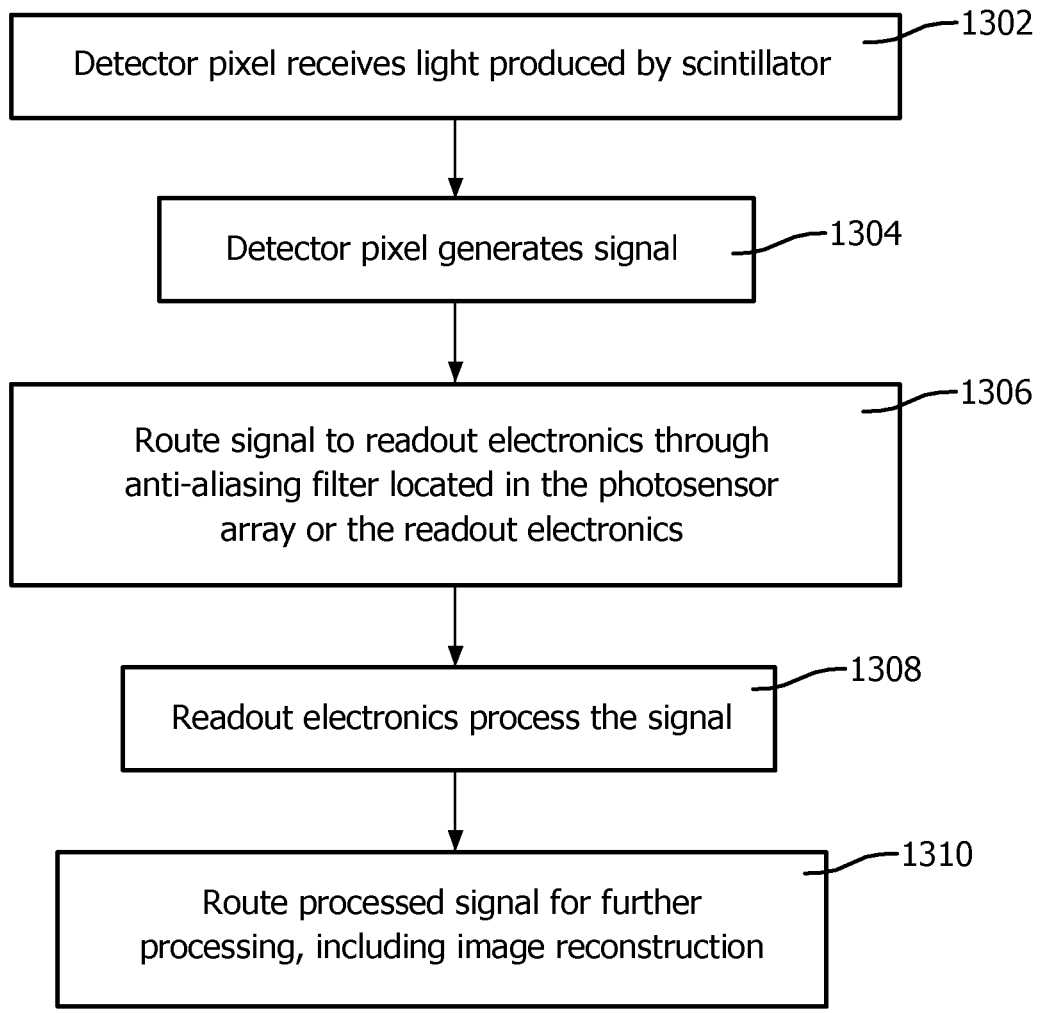

FIG. 13 illustrates an example method.

Figure 4:
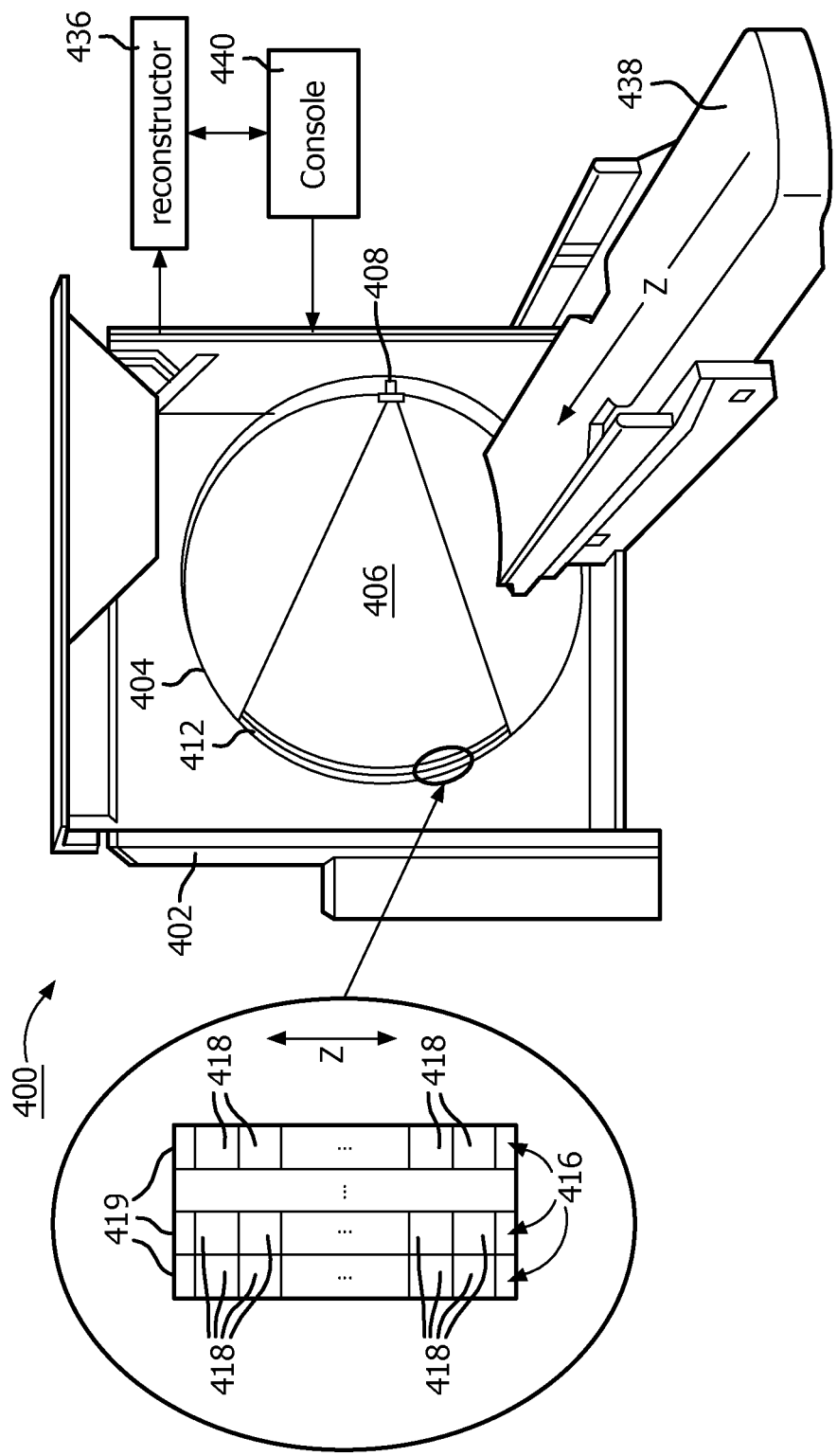
FIG. 4 illustrates an imaging system including a detector tile with at least analog readout electronics electrically isolated on a per pixel basis and including anti-aliasing filtering the ASIC and/or photosensor.

In initially referring to FIG. 4, an imaging system 400, such as a computed tomography (CT) scanner, is illustrated. The imaging system 400 includes a generally stationary gantry 402 and a rotating gantry 404. The rotating gantry 404 is rotatably supported by the stationary gantry 402 and rotates around an examination region 406 about a longitudinal or z-axis. A radiation source 408, such as an x-ray tube, is supported by and rotates with the rotating gantry 404, and produces a generally cone, fan, wedge, or otherwise shaped radiation beam that traverses the examination region 406.

A radiation sensitive detector array 412 subtends an angular arc opposite the radiation sources 408 across the examination region 406 and detects radiation traversing the examination region 406. The radiation sensitive detector array 412 includes one or more rows 416 of detector tiles 418, the rows 416 arranged with respect to each other along the z-axis. The detector tiles 418 are coupled to detector modules 419, via solder balls, stud bumps, and/or otherwise, which are mounted in the system 400, arranged with respect to each other along the z-axis. Briefly turning to FIG. 5, a non-limiting example of a detector tile 418 is illustrated. For clarity and explanatory purposes, the tile 418 is shown in an exploded view in which various components thereof are separated from each other.

The tile 418 includes a scintillator layer 420 optically coupled to a photosensor 422, which includes a plurality of photosensitive areas (detector pixels) 424 within a non-photosensitive area 426 on a first side 428 of the photosensor 422. The illustrated photosensor 422 is a back-illuminated photosensor with electrodes (not visible) that inter-connect the detector pixels 424 to bonding pads or the like (not visible) located on a second opposing side 430 of the photosensor 422. In another embodiment, the photosensor 422 is a front-illuminated photosensor with vias that route the signals from the first side 428 to the pads on the opposing side 430. The scintillator layer 420 may include a plurality of scintillator pixels, each corresponding to one of the detector pixels 424.

An ASIC (readout electronics) 432 includes a plurality of pixel channel wells 434. Each channel well 434 corresponds to only one of the detector pixels 424. A channel well 434 includes one or more electrical components, such as transistors and/or other electronics, for its corresponding detector pixel 424. The illustrated ASIC 432 has a one to one geometric relationship with the photosensor 422, and each channel well 434 has a one to one geometric relationship with a detector pixel 424. That is, surfaces of the ASIC 432 and the photosensor 422 that are bonded are approximately a same size. Likewise, surfaces of a well 434 and detector pixel 424 are approximately the same size. In another embodiment, the surfaces are not the same size, for example, the ASIC 432 is smaller than the photosensor 422.

As described in greater detail below, an individual channel well 434 electrically isolates at least the analog electrical components of a channel from the analog electrical components of the other channels. Isolating the analog electrical components as such mitigates crosstalk between the analog electrical components of the different channels of the different detector pixels 424. This may improve detector linearity, gain, and noise performance, relative to a configuration in which the wells 434 are omitted. This also renders the system 400 well-suited for low-dose imaging.

Also described in greater detail below, in one instance, the ASIC 432 includes an anti-aliasing filter for each detector pixel 424, for example, in one or more metal layers of the ASIC 432 and/or in the wells 434 in regions of the ASIC 432 that otherwise do not include electrical components. As such, anti-aliasing filtering can be provided at the ASIC level, without requiring additional space, which may reduce quantum noise and electronics noise, which allows for lower-dose imaging and improved noise performance relative to a configuration in which the anti-aliasing filters are omitted from the ASIC 432.

The ASIC 432 and the photosensor 422 are bonded together with the ASIC channels 434 in electrical communication with the bonding pads of the photosensor 422. In the illustrated embodiment, both the photosensor 422 and the ASIC 432 include silicon and are bonded together via glue, solder ball, flip chip, covalent bonding, and/or other silicon-to-silicon bonding approaches. An example of semiconductor silicon-to-silicon bonding is discussed in U.S. patent application publication 2009/0121146 to Luhta et al., which is incorporated herein by reference in its entirety. Optionally, an interposer substrate may be placed between the assemblies 422 and 432 with pass-through connections to facilitate assembly at some additional cost.

Returning to FIG. 4, a reconstructor 436 reconstructs the signal from the detector array 412, generating volumetric three-dimensional image data. A support 438, such as a couch, supports the object or subject in the examination region 406. A general purpose computing system serves as an operator console 440, which includes human readable output devices such as a display and/or printer and input devices such as a keyboard and/or mouse. Software resident on the console 440 allows the operator to control the operation of the imaging system 400.

FIG. 6 shows a portion of the ASIC 432. In this example, the ASIC 432 includes at least one analog pixel channel well 602, 604, . . . , and at least one digital common well 606. The ASIC 432 may also include at least one analog common well and/or one or more other wells.

The at least one analog pixel channel well 602 includes a plurality of channels 608, each including an analog N-channel field-effect transistor (NFET) 610, an analog P-type field-effect transistor (PFET) 612, a digital NFET 614, and a digital PFET 616 in an N-type analog channel well. P-type wells and corresponding transistor configurations are also contemplated herein. The at least one common digital well 606 also includes a plurality of channels 618, such as NFETs and PFETs. Likewise, the common digital well 606 may alternatively include a P-type well.

For any given analog pixel channel well, for example, the well 602, the transistors (610-616) therein are electrically isolated from the transistors of another analog channel well, for example, the analog channel well 604. The channel wells 602, 604 and 606 also electrically isolate the transistors therein from a substrate 620, in which the wells 602, 604 and 606 are located. The isolation of circuitry in wells 602, 604 and 606 can be formed via triple-well isolation and/or other known and/or other approaches such as STI (Shallow Trench Isolation) for providing isolation in silicon semiconductor material.

FIG. 7 shows a variation of the portion of the ASIC 432 in which the digital transistor 614 and 616 are located in the digital common well 606 instead of in the analog channel well 602. In this embodiment, the analog transistors 610 and 612 are still located in the analog channel well 602 but the digital transistors 614 and 616 are located in the digital channel well 606. This configuration additionally electrically isolates the analog transistors 610 and 612 and the digital transistors 614 and 616 of a detector pixel.

The configurations shown in FIGS. 6 and 7 at least provide analog channel to analog channel electrical isolation between detector pixels by electrically isolating the analog transistors of the analog channel of one detector pixel from the analog transistors of other analog channels of another detector pixel via analog channels wells (e.g., wells 602 and 604). Such a configuration confines channel activity to a single well, mitigating channel-to-channel crosstalk.

Figure 1:
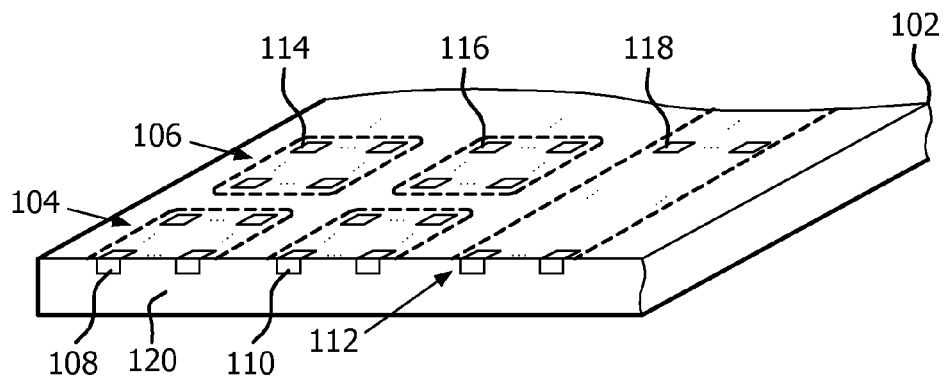
FIG. 1 depicts a portion of a prior art imaging detector ASIC without electrical isolation between analog and digital readout electronics and the substrate.
Figure 2:
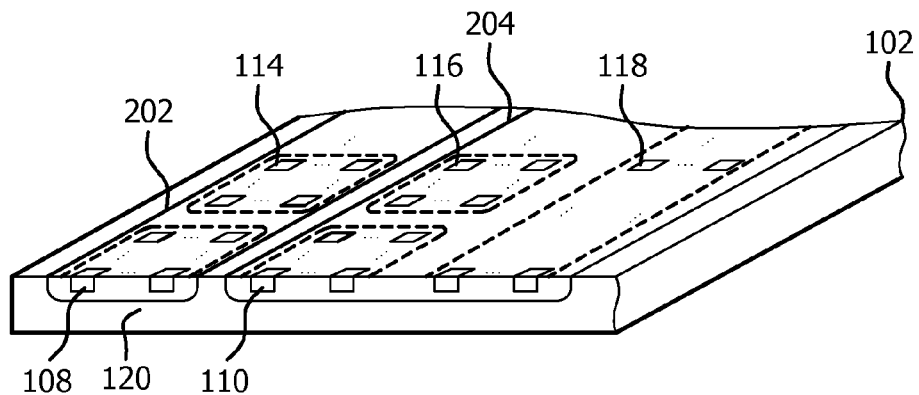
FIG. 2 depicts a portion of a prior art imaging detector ASIC in which analog and digital readout electronics are electrically isolated from each other and the substrate through a common analog well and a common digital well.
Figure 3:
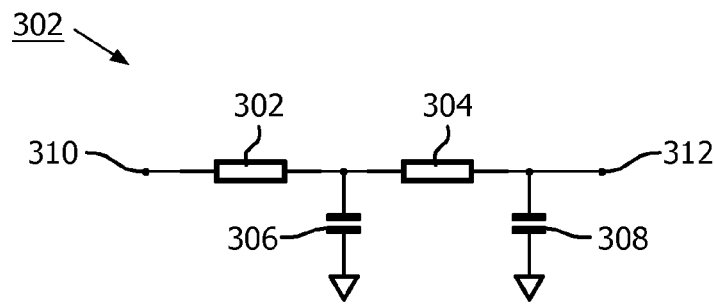
FIG. 3 depicts prior art external anti-aliasing circuitry for the readout electronics of FIG. 1 or 2.

It is to be appreciated that this can improve detector linearity and noise performance relative to a configuration in which the individual channels are not electrically isolated from each other, for example, those shown in connection with FIGS. 1 and/or 2. As shown in FIG. 7, the analog and digital transistors of a channel can also be electrically isolated by separating them into different wells, which mitigates analog and digital noise contamination for a single channel.

FIG. 8 schematically illustrates an embodiment in which the ASIC 432 includes anti-aliasing filters 800 for each detector pixel of the detector pixels 424. For clarity and sake of brevity, only one anti-aliasing filter 800 is shown in connection with a corresponding detector pixel 424 and analog ASIC well 602. However, it is to be understood that the anti-aliasing filters 800 for other detector pixels 424 and wells 602 are similar.

In this example, the ASIC 432 includes a plurality of metal layers 802, including layers $802_1, 802_2, 802_3, 802_4, \ldots, 802_K$ (where K is an integer greater than one) and the anti-aliasing filter 800 is part of the metal layers 802. Each anti-aliasing filter 800 includes a first electrode 804 in the layer $802_4$, a second electrode 806 in the layer $802_2$, an insulating layer 808 disposed there between the layer $802_3$ and including a dielectric material with a dielectric constant, forming a capacitor in the layers 802. Metal-insulator-metal (MIM) and/or other fabrication processes can be used to fabricate the capacitor of the filter 800. Resistors 814 of the filter 800 can be formed in the silicon of the well 602 with electrical interconnects 816 between the capacitor 804/806/808 in the ASIC metal layers 802 and the resistors 814.

The photosensor 422 also includes a plurality of metal layers 810, including layers $810_1, 810_2, 810_3, 810_4, \ldots, 810_L$ (where L is an integer greater than one), which are coupled via a layer 812 to the layers 802 of the ASIC 432 such that the detector pixel 424 is in electrical communication with the readout electronics of the well 602 and 606 through the anti-aliasing filters 800.

FIG. 9 shows a perspective view of the embodiment of FIG. 8, showing an example geometrical relationship between the detector pixel 424, the anti-aliasing filter 800, and the channel well 602. In this embodiment, there is a one to one geometrical relationship between an area 804 of the detector pixel 424 facing an area 804 of the detector well 602 and a one to one geometrical relationship between an area 804 of the detector pixel 424 facing an area 808 of the anti-aliasing filter 800, and hence, a one to one geometrical relationship between an area 810 of the anti-aliasing filter 800 facing an area 804 of the well 602. Non one to one relationships are also contemplated herein.

FIGS. 10 and 11 schematically illustrate a variation of FIGS. 8 and 9 in which the anti-aliasing filter 800 is located in the metal layers 810 of the photosensor array 422 (layers $810_2$, $810_3$ and $810_4$ in this example) instead of the metal layers 802 of the ASIC 432. As shown in FIG. 10, the resistors 814 are in the silicon of the well 602 and the electrical interconnects 816 run between the capacitor 804/806/808 in the photosensor array metal layers 810 and the resistors 814.

FIG. 12 shows an example configuration of the anti-aliasing filter 800, which includes a plurality of sub-capacitors 1202. In this example, a first grouping 1204 of sub-capacitors are electrically connected in parallel to form one of the capacitors of the anti-aliasing filter 800 and a second grouping 1206 of sub-capacitors are electrically connected in parallel to form a second of the capacitors of the anti-aliasing filter 800. In this embodiment, the first capacitor has about ten times the capacitance as the second capacitor, and both groupings 1204 and 1206 have suitable capacitance to form reasonable anti-aliasing filter 800.

In another embodiment, anti-aliasing filters capacitors can be in one or more of the ASIC layers 802, the photosensor layers 810 and/or the channel well 602. Other approaches to implementing the anti-aliasing filter in the ASIC 432 or photosensor 422 are also contemplated herein.

FIG. 13 illustrates a method.

At 1302, a detector pixel of a photosensor array receives light produced by a scintillator in response to detection of x-ray radiation.

At 1304, the detector pixel generates a signal indicative of the received light.

At 1306, the signal is routed to readout electronics corresponding to the detector pixel through an anti-aliasing filter, which is located in the ASIC or photosensor array.

At 1308, the readout electronics processes the signal.

At 1310, the processed signal is routed from the readout electronics to another component for further processing, including reconstruction.

It is to be appreciated that the ordering of the acts in the methods described herein is not limiting. As such, other orderings are contemplated herein. In addition, one or more acts may be omitted and/or one or more additional acts may be included.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging apparatus, comprising:
    a detector array with at least one detector tile, the detector tile, comprising:
        a photosensor array with a two dimensional array of individual photosensitive detector pixels located within a non-photosensitive area;
        readout electronics coupled to the photosensor array and including individual readout channel wells corresponding to the individual detector pixels; and
        an anti-aliasing filter for a detector pixel that is located in at least one of a region of the photosensor array corresponding to the detector pixel or a region of the readout electronics corresponding to the detector pixel.

2. The imaging apparatus of claim 1, wherein a geometry of an anti-aliasing filter is approximately equal to or smaller than a geometry of a detector pixel.

3. The imaging apparatus of claim 1, wherein a geometry of the readout electronics is approximately equal to or smaller than the geometry of the detector pixel.

4. The imaging apparatus of claim 1, the readout electronics, comprising:
    a plurality of metal layers, wherein the anti-aliasing filter is located in the plurality of metal layers of the readout electronics.

5. The imaging apparatus of claim 1, wherein the anti-aliasing filter is located in a corresponding readout channel well.

6. The imaging apparatus of claim 1, the photosensor array, comprising:
    a plurality of metal layers, wherein the anti-aliasing filter is located in the plurality of metal layers of the photo sensor array.

7. The imaging apparatus of claim 4, wherein the anti-aliasing filter includes two capacitors.

8. The imaging apparatus of claim 7, wherein the anti-aliasing filter includes two conductive electrodes separated by an insulator.

9. The imaging apparatus of claim 8, wherein approximately one tenth of each of the two conductive electrodes form one of the capacitors and approximately nine tenths of each of the two conductive electrodes form the other of the capacitors.

10. The imaging apparatus of claim 1, wherein the photosensor array is a silicon photosensor array and the readout electronics are part of a silicon integrated circuit, and the silicon integrated circuit and the photosensor array are bonded through a silicon-to-silicon bond.

11. The imaging apparatus of claim 1, wherein the photosensor array includes back-illuminated photodiodes.

12. The imaging apparatus of claim 1, wherein the photosensor array includes front-illuminated photodiodes.

13. The imaging apparatus of claim 1, wherein the readout electronics and the photosensor array include silicon substrates bonded together through covalent bonding.

14. A method, comprising:
    routing a detector pixel output signal to readout electronics corresponding the detector pixel, which is one of a plurality of detector pixels in a photosensor array of an imaging detector, through an anti-aliasing filter that is located in one of the photosensor array or the readout electronics, wherein the readout electronics of the detector pixel are located in a well corresponding to the detector pixel; and
    processing the signal with the readout electronics.

15. The method of claim 14, wherein a geometry of the readout electronics is approximately equal to or smaller than a geometry of a detector pixel.

16. The method of claim 14, wherein a geometry of an anti-aliasing filter is approximately equal to or smaller than a geometry of a detector pixel.

17. The method of claim 14, wherein the anti-aliasing filter is located in a plurality of metal layers of the readout electronics.

18. The method of claim 14, wherein the anti-aliasing filter is located in the corresponding well.

19. The method of claim 14, wherein the anti-aliasing filter is located in a plurality of metal layers of the photosensor array.

20. An imaging detector array, comprising:
    a photosensor array with a two dimensional array of individual photosensitive detector pixels located within a non-photosensitive area;
    readout electronics coupled to the photosensor array, the readout electronics comprising:
    individual readout channel wells, each well corresponding to an individual detector pixel; and
    an anti-aliasing filter for an individual readout channel well located in one of the photosensor array or the readout electronics.

* * * * *